United States Patent
Bei et al.

(10) Patent No.: US 9,036,138 B2
(45) Date of Patent: May 19, 2015

(54) METHOD AND SYSTEM FOR DETECTING FIBER FAULT IN PASSIVE OPTICAL NETWORK

(75) Inventors: Jinsong Bei, Shenzhen (CN); Jidong Xu, Shenzhen (CN); Jie Su, Shenzhen (CN); Jianxin Lu, Shenzhen (CN)

(73) Assignee: ZTE CORPORATION, Shenzhen, Guangdong Province (CN)

( * ) Notice: Subject to any disclaimer, the term of this patent is extended or adjusted under 35 U.S.C. 154(b) by 158 days.

(21) Appl. No.: 13/818,937

(22) PCT Filed: Jun. 27, 2011

(86) PCT No.: PCT/CN2011/076448
§ 371 (c)(1),
(2), (4) Date: Feb. 25, 2013

(87) PCT Pub. No.: WO2012/024977
PCT Pub. Date: Mar. 1, 2012

(65) Prior Publication Data
US 2013/0148109 A1      Jun. 13, 2013

(30) Foreign Application Priority Data

Aug. 25, 2010   (CN) .......................... 2010 1 0263174

(51) Int. Cl.
| | |
|---|---|
| *G01N 21/00* | (2006.01) |
| *H04B 17/00* | (2006.01) |
| *G01N 21/958* | (2006.01) |
| *G01M 11/00* | (2006.01) |

(Continued)

(52) U.S. Cl.
CPC ......... *G01N 21/958* (2013.01); *G01M 11/3136* (2013.01); *G01M 11/3109* (2013.01); *H04B 10/071* (2013.01); *H04B 10/272* (2013.01); *H04J 14/0282* (2013.01); *H04J 14/0295* (2013.01)

(58) Field of Classification Search
None
See application file for complete search history.

(56) References Cited

U.S. PATENT DOCUMENTS

| | | | | |
|---|---|---|---|---|
| 5,491,573 | A * | 2/1996 | Shipley | ........................... 398/13 |
| 6,396,573 | B1 * | 5/2002 | Pimpinella | ................... 356/73.1 |

(Continued)

FOREIGN PATENT DOCUMENTS

| | | |
|---|---|---|
| CN | 101304283 A | 11/2008 |
| CN | 101442691 A | 5/2009 |

(Continued)

OTHER PUBLICATIONS

International Search Report (Form PCT/ISA/210) for PCT/CN2011/076448, mailed Oct. 20, 2011.

*Primary Examiner* — Gordon J Stock, Jr.
(74) *Attorney, Agent, or Firm* — Koppel, Patrick, Heybl & Philpott

(57) ABSTRACT

The disclosure provides a method and a system for detecting a fiber fault in a Passive Optical Network (PON). The system comprises an optical path detection device, a Wavelength Division Multiplexing (WDM) coupler, a wavelength selection coupler, a branch fiber selector and a wavelength selection router. The detection system is attached to an original PON system, without influencing the operation of the original system while performing the detection. With the disclosure, the problem of being unable to determine whether there is a fault in a branch fiber due to the loss of an optical path detection reflection signal is solved, the branch fiber with a fault can be quickly located and fixed, thus the operational and maintenance costs of an operator are reduced.

11 Claims, 5 Drawing Sheets

(51) Int. Cl.
*H04B 10/071* (2013.01)
*H04B 10/272* (2013.01)
*H04J 14/02* (2006.01)

(56) References Cited

U.S. PATENT DOCUMENTS

| | | | |
|---|---|---|---|
| 6,396,575 B1 * | 5/2002 | Holland | 356/73.1 |
| 6,534,997 B1 * | 3/2003 | Horishita et al. | 324/534 |
| 7,684,702 B2 * | 3/2010 | Lu | 398/67 |
| 7,800,744 B2 * | 9/2010 | Lai et al. | 356/73.1 |
| 8,077,298 B2 * | 12/2011 | Wang et al. | 356/73.1 |
| 8,411,259 B2 * | 4/2013 | Levin et al. | 356/73.1 |
| 8,452,173 B2 * | 5/2013 | Hehmann et al. | 398/25 |
| 8,693,866 B1 * | 4/2014 | Lam et al. | 398/21 |
| 8,724,102 B2 * | 5/2014 | Urban | 356/73.1 |
| 2004/0207923 A1 * | 10/2004 | Kachru et al. | 359/634 |
| 2006/0029390 A1 * | 2/2006 | Schmuck et al. | 398/33 |
| 2006/0110161 A1 * | 5/2006 | Cho et al. | 398/72 |
| 2008/0031624 A1 * | 2/2008 | Smith et al. | 398/71 |
| 2011/0255860 A1 * | 10/2011 | Lee et al. | 398/12 |
| 2014/0111795 A1 * | 4/2014 | Barnhart et al. | 356/73.1 |

FOREIGN PATENT DOCUMENTS

| | | |
|---|---|---|
| CN | 101924590 A | 12/2010 |
| CN | 101924962 A | 12/2010 |
| CN | 101984561 A | 3/2011 |
| CN | 102098098 A | 6/2011 |

* cited by examiner

METHOD AND SYSTEM FOR DETECTING FIBER FAULT IN PASSIVE OPTICAL NETWORK

TECHNICAL FIELD

The disclosure relates to the field of communications, and in particular to a method and a system for detecting a fiber fault in a Passive Optical Network (PON).

BACKGROUND

With rapid development of network techniques and popularization of network applications, for example, network communications, online shopping, network entertainment and the like have become a part of modern people's life. An existing access network copper wire (wired) system can not meet the requirement of this high speed and broad band. However, a PON which has advantages of broad band, high speed, environment friendliness and energy conservation is a best option for replacing the existing access network. At present, the PON is being accepted and provided by most operators for satisfying growing communication users and meeting faster and better service requirements.

The PON is a point-to-multipoint fiber access technology. As shown in FIG. 1, the PON comprises an Optical Line Terminal (OLT), an Optical Network Unit (ONU) and an Optical Distribution Network (ODN), wherein the point-to-multipoint structure of the PON generally is formed by coupling one OLT with a plurality of ONUs through an optical power splitter (optical splitter for short) of the ODN.

After the setup and deployment of a large number of PONs, it is needed to consider the operation and maintenance of the network, especially detection of a fiber line and location of a fault. In order to reduce operation and maintenance costs, operators expect to adopt at the OLT an optical path detection device, also called an Optical Time Domain Reflectometer (OTDR), to detect a trunk fiber and branch fibers of the entire PON. If one branch fiber has a fault, it is expected to find and locate the fault and to perform maintenance quickly without influencing services of other branch fibers.

When one OTDR is adopted at a central office OLT to detect this point-to-multipoint network, it can be accurately detected whether the trunk fiber is normal; however, when detecting a signal of the branch fiber, two problems as follows would be encountered.

1. If part branch fibers have approximately equal distance to the optical splitter, the OTDR can not distinguish which branch fiber the signal is from, except that a high resolution OTDR is adopted. However, the highest resolution that can be provided at present is 2 meters, which still can not meet the actual needs.

2. If a splitting ratio of the optical splitter is very large, a Rayleigh reflection signal of the branch fiber would suffer great loss when passing through the optical splitter. When the reflection signal arrives at the OTDR, the reflection signal is mixed with noises and is difficult to be distinguished.

For example, for a 10-kilometer ODN with a splitting ratio of 1:32, the loss of the optical splitter is 3*5+3=18 dB, while the loss of a 10-kilometer fiber is 0.40*10=4.0 dB. Generally, the widest dynamic range of the OTDR is about 40 dB. For example, when a signal of the OTDR passes through the optical splitter and reaches a tail end of the branch fiber, and then is totally reflected (that is, reflection loss is not counted) to the OTDR via the optical splitter, if other loss (for example, connection loss) is not counted, then the maximum full path loss of the signal of the OTDR would be 2*18+2*4.0=44 dB, which already exceeds the work dynamic range of the OTDR; therefore, the signal of the branch fiber is submerged in noises. Thus, it can be seen that the conventional OTDR adopted at the central office can not measure the fault of the branch fiber of the ODN with a large splitting ratio. This phenomenon is very popular. In an actual PON network, due to various reasons, even in the PON with a very small splitting ratio, the reflection signal of the branch fiber can not be obtained by a common OTDR.

In view of the problems above, an existing solution is to add one optical filter before each ONU, refer to FIG. 2. This filter transmits all lights with wavelength less than 1625 nm, but reflects lights transmitted by the OTDR with wavelength greater than 1625 nm. After the optical filter is adopted, the light reflected by a port can be enhanced by 6 dB, and in the cooperation of a high-resolution OTDR, it can be determined whether there is a fault in the branch fiber based on whether there are reflected lights. However, when there is a fault in the branch fiber, since the reflected light on the branch fiber is not enhanced by the optical filter, the above phenomenon that the reflected light is submerged in noises still exists; therefore, the exact position of the fault on the branch fiber can not be determined. In addition, if there are part branch fibers having basically equal lengths, the reflected lights basically are overlapped, even the high-resolution OTDR can not distinguish which branch fiber the reflected light is received from. What is worse, for the ODN with a large splitting ratio (for example, greater than 1:128), the gain brought by the filter probably is far less than enough to compensate the loss caused by the optical splitter. Therefore, the OTDR at the central office probably can not receive any information from the branch fiber; consequently, it can not be determined whether there is a fault in the branch fiber and the specific location of the fault can not be determined.

SUMMARY

The disclosure provides a method and a system for detecting a fiber fault in a PON, so as to solve the above problem of being unable to determine whether there is a fault in a branch fiber.

According to one aspect of the disclosure, a system for detecting a fiber fault in a PON is provided, which comprises: an Optical Time Domain Reflectometer (OTDR), which is configured to transmit an optical path detection signal of which a wavelength corresponds to a branch fiber, receive an optical path detection reflection signal, and determine whether there is a fault in a trunk fiber or in the branch fiber according to a state of the optical path detection reflection signal; a Wavelength Division Multiplexing (WDM) coupler, which is configured to import the optical path detection signal onto the trunk fiber and transmit the optical path detection reflection signal transmitted by the trunk fiber to the OTDR; a wavelength selection coupler, which is configured to transmit the optical path detection signal which is on the trunk fiber to a branch fiber selector and import the optical path detection reflection signal, which is received from the branch fiber selector, back onto the trunk fiber; the branch fiber selector, which is configured to transmit the optical path detection signal to a corresponding wavelength selection router and transmit the optical path detection reflection signal, which is transmitted from the wavelength selection router, to the wavelength selection coupler; and the wavelength selection router, which is coupled with a Optical Network Unit (ONU) corresponding to the wavelength selection router through a branch fiber, and is configured to transmit the optical path detection signal to the ONU and transmit the optical path detection reflection signal which is on the branch fiber to the branch fiber selector.

Preferably, the WDM coupler is further configured to receive a downlink signal of an Optical Line terminal (OLT) and import the downlink signal onto the trunk fiber, separate the optical path detection reflection signal and an uplink signal that are transmitted by the trunk fiber, and transmit the uplink signal to the OLT; the wavelength selection coupler is further configured to separate the optical path detection signal and the downlink signal that are transmitted by the trunk fiber, transmit the downlink signal to an optical splitter, receive the uplink signal transmitted by the optical splitter and transmit the uplink signal to the trunk fiber; the system further comprises: the optical splitter, which is configured to transmit the downlink signal to all wavelength selection routers, receive the uplink signal transmitted by each wavelength selection router and transmit the uplink signal to the wavelength selection coupler; the wavelength selection router is further configured to transmit the downlink signal to the ONU which is coupled with the wavelength selection router, separate the optical path detection reflection signal and the uplink signal of the ONU, and transmit the separated uplink signal to the optical splitter.

Preferably, the WDM coupler is a first optical filter, and the first optical filter comprises: a first interface, which is coupled with the OLT and is configured to transmit the uplink signal and the downlink signal; a second interface, which is coupled with the OTDR and is configured to: transmit the optical path detection signal to the trunk fiber and transmit the optical path detection reflection signal to the OTDR; and a general interface, which is coupled with the trunk fiber.

Preferably, the wavelength selection coupler is a second optical filter, and the second optical filter comprises: a first interface, which is coupled with the optical splitter and is configured to transmit the uplink signal and the downlink signal; a second interface, which is coupled with the branch fiber selector and is configured to: transmit the optical path detection signal to the branch fiber selector and transmit the optical path detection reflection signal to the trunk fiber; and a general interface, which is coupled with the trunk fiber.

Preferably, the branch fiber selector is an Arrayed-Waveguide Grating (AWG), and the AWG comprises: a general interface, which is coupled with the wavelength selection coupler; a plurality of grating branch inputs/outputs, which are coupled with the wavelength selection router on each branch fiber and are configured to transmit the optical path detection signal to the corresponding wavelength selection router according to the wavelength of the optical path detection signal.

Preferably, the wavelength selection router is a third optical filter, and the third optical filter comprises: a first interface, which is coupled with the optical splitter and is configured to transmit the uplink signal and the downlink signal; a second interface, which is coupled with the branch fiber selector and is configured to: receive the optical path detection signal and transmit the optical path detection reflection signal to the branch fiber selector; and a general interface, which is coupled with the ONU through the branch fiber and is configured to: transmit the optical path detection signal received by the second interface to the ONU and receive the optical path detection reflection signal from the branch fiber.

Preferably, the first optical filter, the second optical filter and the third optical filter are thin film filters, wherein the thin film filters reflect a signal with an optical path detection wavelength and transmit a signal with a wavelength other than the optical path detection wavelength.

According to another aspect of the disclosure, a method for detecting fiber fault in a Passive Optical Network (PON) is provided, comprising: an Optical Time Domain Reflectometer (OTDR) transmitting an optical path detection signal of which a wavelength corresponds to a branch fiber; a Wavelength Division Multiplexing (WDM) coupler receiving the optical path detection signal and transmitting the optical path detection signal to a wavelength selection coupler through a trunk fiber; the wavelength selection coupler transmitting the optical path detection signal to a corresponding wavelength selection router through a branch fiber selector; the corresponding wavelength selection router transmitting the optical path detection signal to an Optical Network Unit (ONU) through a branch fiber; wherein the optical path detection signal generates an optical path detection reflection signal during a transmission process, and the optical path detection reflection signal is transmitted to the OTDR along an optical path opposite to that of the optical path detection signal; the OTDR determining whether there is a fault in the trunk fiber or in the branch fiber according to a state of the optical path detection reflection signal.

Preferably, a process of the WDM coupler receiving the optical path detection signal further comprises: the WDM coupler receiving a downlink signal of an OLT and importing the downlink signal onto the trunk fiber; a process of the wavelength selection coupler transmitting the optical path detection signal to the corresponding wavelength selection router through the branch fiber selector comprises: the wavelength selection coupler separating the optical path detection signal and the downlink signal that are transmitted by the trunk fiber, transmitting the downlink signal to an optical splitter which then transmits the downlink signal to all wavelength selection routers, and transmitting the optical path detection signal to the wavelength selection router corresponding to the wavelength of the optical path detection signal through the branch fiber selector; a process of the wavelength selection router transmitting the optical path detection signal to the ONU through the branch fiber comprises: the wavelength selection router transmitting, through a connected branch fiber, the downlink signal to the ONU coupled with the wavelength selection router.

Preferably, the method further comprises: the wavelength selection router separating the optical path detection reflection signal and an uplink signal of the ONU, wherein the separated uplink signal is transmitted to the OLT along an optical path opposite to that of the downlink signal.

With the disclosure, the wavelength selection coupler is used to forward the optical path detection signal on the trunk fiber to the branch fiber selector, rather than to the optical splitter, thereby avoiding the loss of the optical path detection signal caused by the optical splitter. Meanwhile the wavelength selection router is used to forward the optical path detection reflection signal which is on the branch fiber to the branch fiber selector, thus the problem of being unable to determine whether there is a fault in the branch fiber due to the loss of the optical path detection reflection signal is solved, the branch fiber with a fault can be quickly located and fixed, and the operational and maintenance costs of an operator are reduced.

BRIEF DESCRIPTION OF THE DRAWINGS

Drawings, provided for further understanding of the disclosure and forming a part of the specification, are used to explain the disclosure together with embodiments of the disclosure rather than to limit the disclosure, wherein.

DETAILED DESCRIPTION OF THE EMBODIMENTS

The disclosure is described below in detail by reference to the accompanying drawings in conjunction with embodiments. It should be noted that the embodiments in the application and the characteristics of the embodiments can be combined if no conflict is caused.

An optical network system in the embodiments of the disclosure comprises an ONU, an ODN and an OLT, wherein each device in the system is interconnected through a fiber. The following embodiments are described by taking the implementation in this system for example.

Embodiment 1

Figure 1:
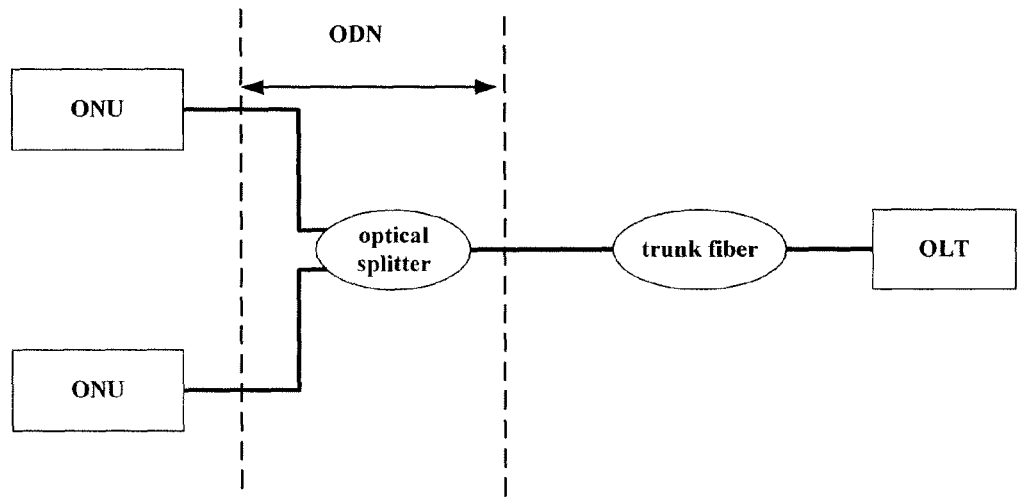
FIG. 1 shows a structure diagram of a PON according to related art.
Figure 2:
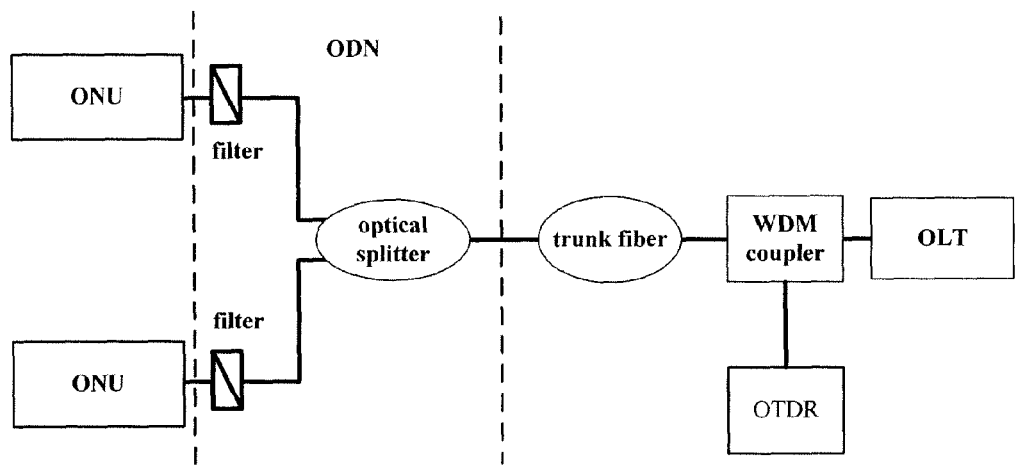
FIG. 2 shows a structure diagram of an optical path detection PON system according to related art.
Figure 3:
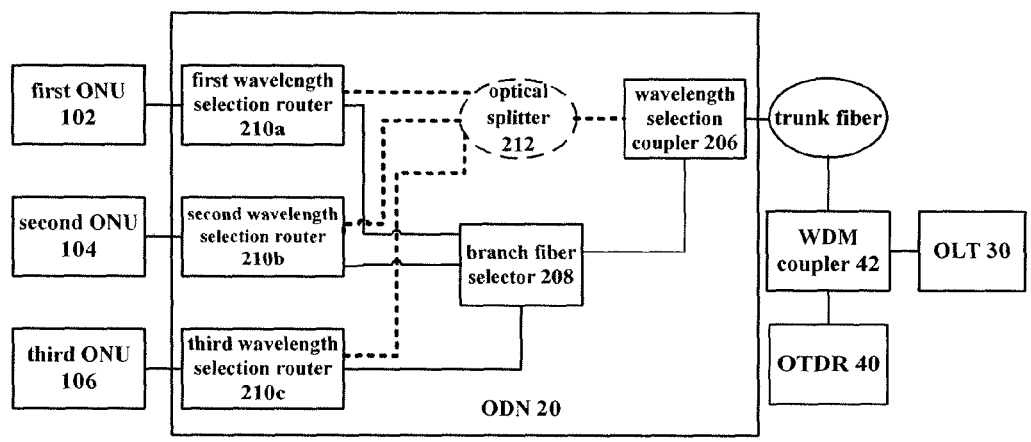
FIG. 3 shows a structure diagram of a system for detecting a fiber fault in a PON according to Embodiment 1 and Embodiment 2 of the disclosure.

FIG. 3 shows a structure diagram of a system for detecting a fiber fault in a PON according to the embodiment of the disclosure. This embodiment is described by taking the PON consisting of three ONUs for example, wherein the ONUs are a first ONU 102, a second ONU 104 and a third ONU 106, respectively. The system also comprises an ODN 20 and an OLT 30.

In this detection system, a WDM coupler 42 is inserted at the OLT 30, so that an OTDR 40 can be coupled with the OLT 30 through the WDM coupler 42; three optical modules, i.e. a wavelength selection coupler 206, a branch fiber selector 208 and a wavelength selection router, are inserted at the ODN 20, wherein the wavelength selection router one-to-one corresponds to the ONU, in this embodiment, the wavelength selection router comprises a first wavelength selection router 210a, a second wavelength selection router 210b and a third wavelength selection router 210c.

The features and functions of each device above are described as follows.

The OTDR 40 is configured to transmit an optical path detection signal of which a wavelength corresponds to a branch fiber, receive an optical path detection reflection signal, and determine whether there is a fault in a trunk fiber or in the branch fiber according to a state of the optical path detection reflection signal.

The WDM coupler 42 is configured to import the optical path detection signal onto the trunk fiber and transmit the optical path detection reflection signal transmitted by the trunk fiber to the OTDR 40.

The wavelength selection coupler 206 is configured to transmit the optical path detection signal which is on the trunk fiber to the branch fiber selector 208 and import the optical path detection reflection signal, which is received from the branch fiber selector 208, back to the trunk fiber.

The branch fiber selector 208 is configured to transmit the optical path detection signal to a corresponding wavelength selection router and transmit the optical path detection reflection signal transmitted from the wavelength selection router to the wavelength selection coupler 206. The wavelength selection router one-to-one corresponds to the ONU, in this embodiment, the wavelength selection router comprises the first wavelength selection router 210a, the second wavelength selection router 210b and the third wavelength selection router 210c, which have the same functions. This embodiment is described by taking the corresponding wavelength selection router being the first wavelength selection router 210a for example.

The first wavelength selection router 210a is coupled with the first ONU 102 through a branch fiber, and is configured to transmit the optical path detection signal to the first ONU 102 and transmit the optical path detection reflection signal on the branch fiber to the branch fiber selector 208.

The WDM coupler 42, the wavelength selection coupler 206 and the wavelength selection router (210a, 210b and 210c) all may be thin film filters, for example, they all are sideband type thin film filters. If an optical path detection wavelength is selected to be at U band, that is, from 1625 nm to 1675 nm, then a sideband filter is selected as the thin film filter, that is, to reflect signals with wavelength greater than 1625 nm and to transmit signals with wavelength less than 1625 nm; meanwhile, an AWG in the branch fiber selector is selected to work in U band too. If the optical path detection wavelength is selected to be at C band, that is, from 1528 nm to 1560 nm, then a broadband filter is selected as the thin film filter, that is, to reflect signals with wavelength in C band and to transmit signals with wavelength not in C band; meanwhile, the AWG in the branch fiber selector is selected to work in C band too.

In the detection system shown in FIG. 3, an optical splitter 212 is provided between the wavelength selection coupler 206 and the wavelength selection router (the first wavelength selection router 210a, the second wavelength selection router 210b and the third wavelength selection router 210c), wherein the optical splitter 212 and the connection line between this optical splitter and other devices are represented by dash line, to indicate that the optical splitter 212 does not transmit the optical path detection signal and the optical path detection reflection signal, but transmits an uplink signal and a downlink signal only.

The OTDR 40 is a device with optical wavelength tunable; the wavelength of the corresponding optical path detection signal transmitted by the OTDR 40 can be adjusted according to the branch fiber to be detected, so that optical path detection signals of different wavelengths are transmitted along different branch fibers, thus the purpose of detecting whether there is a fault in this branch fiber can be achieved.

In this embodiment, although each branch fiber has a wavelength selection router connected therewith, not every wavelength selection router transmits the optical path detection signal. In this embodiment, the branch fiber selector selects a wavelength selection router which corresponds to the wavelength of the optical path detection signal to transmit the optical path detection signal, and other wavelength selection routers do not transmit the optical path detection signal. The branch fiber selector in this embodiment can turn off a channel which does not correspond to the wavelength since this channel causes great loss to the light of this wavelength.

In this embodiment, the wavelength selection coupler 206 is used to forward the optical path detection signal which is on the trunk fiber to the branch fiber selector 208, rather than to the optical splitter, thereby avoiding the loss of the optical path detection signal caused by the optical splitter. Meanwhile the wavelength selection router is used to forward the optical path detection reflection signal which is on the branch fiber to the branch fiber selector 208, thereby avoiding the loss of the optical path detection reflection signal caused by the optical splitter. As a result, the intensity of the optical path detection reflection signal is guaranteed to the greatest extent, the problem of being unable to determine whether there is a fault in the branch fiber due to the loss of the optical path detection reflection signal is solved, and the specific location of the fault can be determined according to the time when an abnormality occurs to the optical path detection reflection signal.

Embodiment 2

The detection system shown in FIG. 3 mentioned in the above Embodiment 1 can be attached to an original PON system, without influencing the operation of the original system while performing the detection. Hereinafter, description is provided by taking the system for detecting a fiber fault in the PON shown in FIG. 3 for example, and this embodiment mainly describes the operation process of the optical path detection signal and a communication signal.

From FIG. 3, it can be known that the system comprises: an OTDR 40 with wavelength tunable, a WDM coupler 42, a wavelength selection coupler 206, a branch fiber selector 208, and at least one wavelength selection router coupled with an optical splitter 212. In this embodiment, the wavelength selection router comprises a first wavelength selection router 210a, a second wavelength selection router 210b and a third wavelength selection router 210c.

The WDM coupler 42 is coupled with the OTDR 40 and an OLT 30, and is coupled with the wavelength selection coupler 206 through a trunk fiber.

The wavelength selection coupler 206 is coupled with the optical splitter 212 and the branch fiber selector 208.

The branch fiber selector 208 is coupled with each wavelength selection router, that is, the branch fiber selector 208 is coupled with the first wavelength selection router 210a, the second wavelength selection router 210b and the third wavelength selection router 210c in this embodiment.

Each wavelength selection router is coupled with an ONU through a corresponding branch fiber, respectively. In this embodiment, the ONU comprises a first ONU 102, a second ONU 104 and a third ONU 106. As shown in FIG. 3, the first wavelength selection router 210a is coupled with the first ONU 102 through a first branch fiber; the second wavelength selection router 210b is coupled with the second ONU 104 through a second branch fiber, and the third wavelength selection router 210c is coupled with the third ONU 106 through a third branch fiber.

The OTDR 40 is configured to transmit to the WDM coupler 42 an optical path detection signal with a specific wavelength used for a corresponding branch fiber, and determine whether there is a fault in the trunk fiber and the corresponding branch fiber by analyzing whether the received optical path detection reflection signal is abnormal.

The optical path detection reflection signal may be a Fresnel reflection signal or a Rayleigh reflection signal. When this signal has an abrupt change, it can be determined that there is a fault in the trunk fiber or in the corresponding branch fiber, and the specific location of the fault can be determined according to the occurrence moment of the abrupt change and the transmission speed of the signal.

The WDM coupler 42 is configured to import the received optical path detection signal and the downlink signal of the OLT 30 onto the trunk fiber, transmit the separated optical path detection reflection signal of the trunk fiber to the OTDR 40, and transmit the separated uplink signal to the OLT 30.

The wavelength selection coupler 206 is configured to separate the optical path detection signal from the downlink signal on the trunk fiber, transmit the optical path detection signal to the branch fiber selector 208, transmit the rest downlink signal to the optical splitter 212, import the optical path detection reflection signal, which is received from the branch fiber selector 208, back to the trunk fiber, and meanwhile transmit the uplink signal passing through the optical splitter 212 to the trunk fiber.

The branch fiber selector 208 is configured to guide the optical path detection signal to a related output according to the wavelength of the optical path detection signal, so that the signal enters a wavelength selection router coupled with the branch fiber selector 208, and transmit the optical path detection reflection signal of the branch fiber from the wavelength selection router to the wavelength selection coupler 206. This embodiment is described by taking the transmission of the optical path detection signal to the first wavelength selection router 210a for example.

The optical splitter 212 is configured to transmit the downlink signal to all wavelength selection routers connected therewith, receive the uplink signal transmitted by all the wavelength selection routers, and transmit the uplink signal to the wavelength selection coupler 206.

The wavelength selection router (that is, the first wavelength selection router 210a, the second wavelength selection router 210b and the third wavelength selection router 210c in this embodiment) is configured to transmit to the branch fiber the downlink signal from the optical splitter 212, wherein the second wavelength selection router 210b and the third wavelength selection router 210c in this embodiment are further configured to transmit the uplink signal which is on the branch fiber to the optical splitter 212; the first wavelength selection router 210a is further configured to separate out the optical path detection reflection signal from the uplink signal on the branch fiber and transmit the separated optical path detection reflection signal to the branch fiber selector 208, and transmit the rest separated uplink signal to the optical splitter 212.

In order to import and export the optical path detection signal without influencing the normal service, the WDM coupler 42 is provided at a central office OLT 30 in this embodiment.

Figure 4:
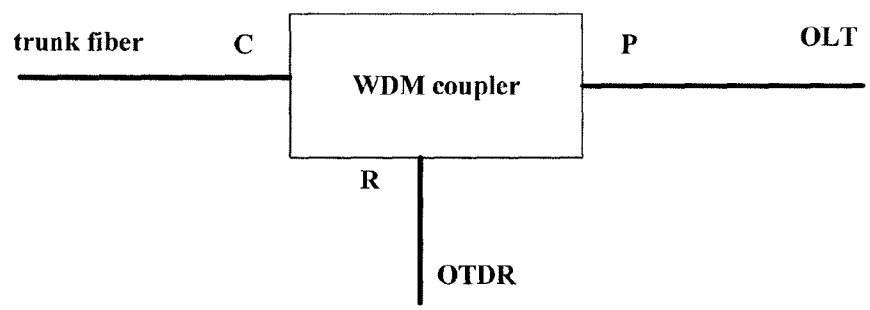
FIG. 4 shows a structure diagram of a WDM coupler according to Embodiment 2 of the disclosure.

Referring to FIG. 4, the WDM coupler 42 may consist of one Thin Film Filter (TFF). This thin film filter reflects all lights with an optical path detection wavelength, but transmits all lights with a wavelength other than the optical path detection wavelength.

The thin film filter comprises: a first interface (represented by P), which is coupled with the OLT 30 and is configured to transmit the uplink signal and the downlink signal, in this embodiment, the wavelength of both uplink signal and downlink signal is less than that of the optical path detection signal;

a second interface (represented by R), which is coupled with the OTDR 40 and is configured to: transmit the optical path detection signal to the trunk fiber and transmit the optical path detection reflection signal to the OTDR 40; and a general interface (represented by C), which is coupled with the trunk fiber.

The thin film filter is configured to import the optical path detection signal output by the OTDR 40 to the trunk fiber, and transmit the optical path detection reflection signal to the OTDR 40, and meanwhile guarantee the communication of normal uplink and downlink signals between the OLT 30 and the ONU.

Figure 5:
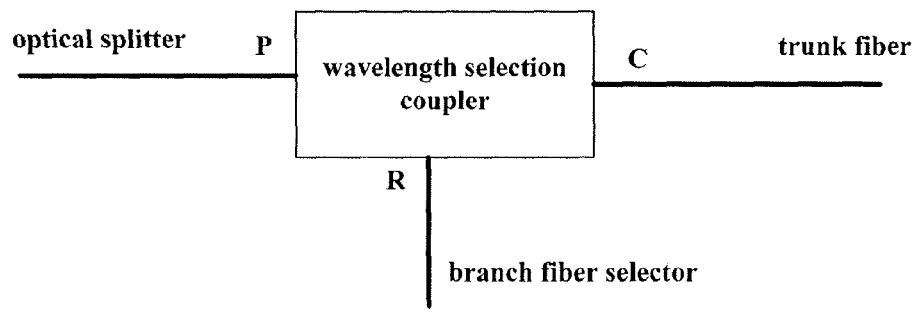
FIG. 5 shows a structure diagram of a wavelength selection coupler according to Embodiment 2 of the disclosure.

In the embodiment of the disclosure, the wavelength selection coupler 206 is provided at the entrance of the optical splitter 212, referring to FIG. 5. The wavelength selection coupler 206 may consist of one thin film filter (TFF). This thin film filter reflects all lights with an optical path detection wavelength, but transmits all lights with a wavelength other than the optical path detection wavelength.

The thin film filter comprises: a first interface (represented by P), which is coupled with the optical splitter 212 and is configured to transmit the uplink signal and the downlink signal, in this embodiment, the wavelength of both uplink signal and downlink signal is less than that of the optical path detection signal;

a second interface (represented by R), which is coupled with the branch fiber selector 208 and is configured to: transmit the optical path detection signal to the branch fiber selector 208 and transmit the optical path detection reflection signal to the trunk fiber; and a general interface (represented by C), which is coupled with the trunk fiber.

The thin film filter is configured to import the optical path detection signal onto the branch fiber selector, and transmit the optical path detection reflection signal of the branch fiber back onto the trunk fiber, and meanwhile guarantee the communication of normal uplink and downlink signals between the OLT 30 and the ONU.

Figure 6:
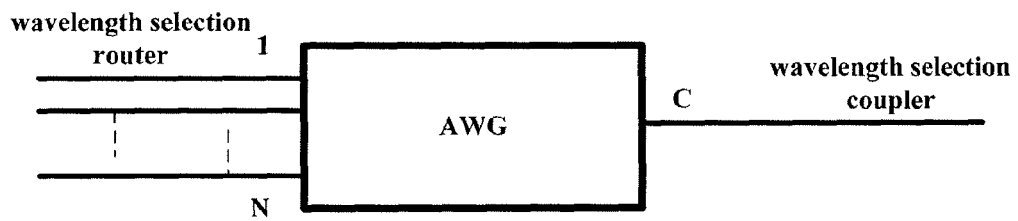
FIG. 6 shows a structure diagram of a branch fiber selector according to Embodiment 2 of the disclosure.

A branch fiber selector 208 is provided beside the optical splitter 212 of the ODN 20, and the branch fiber selector 208 is a passive device. Referring to FIG. 6, the branch fiber selector 208 consists of an AWG, wherein the AWG comprises:

a general interface (represented by C), which is coupled with the wavelength selection coupler 206;

a plurality of grating branch inputs/outputs (represented by 1 to N), which are coupled with the wavelength selection router on each branch fiber and are configured to transmit the optical path detection signal to the corresponding wavelength selection router according to the wavelength of the optical path detection signal.

In order to make the branch fiber selector 208 really passive, the AWG should be irrelevant to environment temperature, that is, the change of the environment temperature, for example, from −20 DEG C. to 60 DEG C., has no impact on the operation parameter and performance of the AWG; otherwise, the AWG needs a temperature control device to keep the operation stable. The selection of working wavelength range of the AWG is relevant to the tunable range of the OTDR used by a user. In order to reduce the interference to the operation of the PON, the wavelength of the AWG needs to avoid the band of uplink and downlink wavelengths. According to the regulation of the wavelength of the OTDR in ITU-T L.66, generally, the working wavelength range is at U band, that is, from 1625 nm to 1675 nm. If necessary, the working wavelength also can select C band or other bands, only if it avoids the normal working band of the PON; in this condition, the filter above and the OTDR also need corresponding adjustment. The channel interval of the AWG generally is 100 GHz, and an AWG with a channel interval of 50 GHz also may be selected if needed. The number of channels of the AWG should be selected corresponding to the splitting number of the optical splitter 212, for example, the ODN with a splitting ratio of 1:32 needs to be provided with a 32-channel AWG. The basic working principle is that optical signals of different wavelengths are transmitted through different channels in the AWG, and the channel of each optical signal is coupled with the branch fiber through the wavelength selection router; in this way, the branch fiber is marked by the wavelength of the optical path detection signal of the OTDR, that is, optical path detection signals of different wavelengths detect the respective branch fibers corresponding to respective optical path detection signals.

Figure 7:
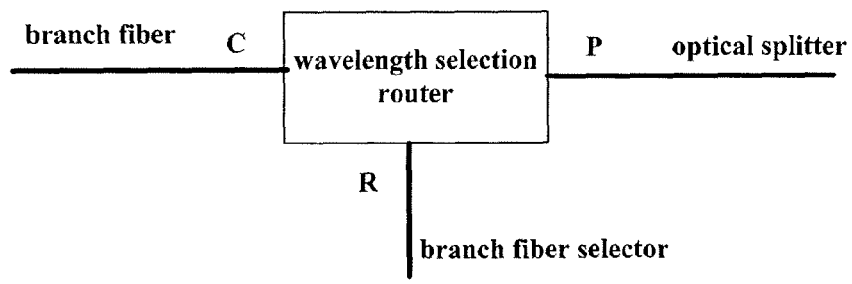
FIG. 7 shows a structure diagram of a wavelength selection router according to Embodiment 2 of the disclosure.

In this embodiment, one wavelength selection router is connected before each branch fiber of the optical splitter 212. Referring to FIG. 7, the wavelength selection router of this embodiment may consist of one thin film filter (TFF). This thin film filter reflects all lights with wavelength greater than 1625 nm (the wavelength of the OTDR), but transmits all lights with wavelength less than 1625 nm.

The thin film filter comprises: a first interface (represented by P), which is coupled with the optical splitter 212 and is configured to transmit the uplink signal and the downlink signal, in this embodiment, the wavelength of both uplink signal and downlink signal is less than that of the optical path detection signal;

a second interface (represented by R), which is coupled with the branch fiber selector 208 and is configured to: receive the optical path detection signal and transmit the optical path detection reflection signal to the branch fiber selector 208; and a general interface (represented by C), which is coupled with the ONU through the branch fiber and is configured to: transmit the optical path detection signal received by the second interface to the ONU, and receive the optical path detection reflection signal from the branch fiber.

The thin film filter is configured to import the optical path detection signal, which is from the branch fiber selector 208, onto the branch fiber, and import the optical path detection reflection signal of the branch fiber back onto the branch fiber selector 208, and meanwhile guarantee the communication of normal uplink and downlink signals between the OLT 30 and the ONU.

The WDM coupler 42, the wavelength selection coupler 206 and the wavelength selection router (210*a*, 210*b* and 210*c*) all adopt the same type of thin film filter, wherein this thin film filter reflects signals with wavelength greater than 1625 nm and transmits signals with wavelength less than 1625 nm. This selection mode simplifies the design of the system and reduces cost.

Through the optical path detection system consisting of the series of auxiliary optical functional modules above, this embodiment can detect and locate the fault of the trunk fiber and any branch fiber intelligently and quickly by using a tunable OTDR at the central office. Moreover, optical path detection signals of different wavelengths are selected to detect related branch fibers, thus the problem of failing in distinguishing the branch fibers with equal lengths caused by the signal overlapping of the branch fibers with equal lengths is avoided. Meanwhile, the optical path detection signal and the optical path detection reflection signal are transmitted to the trunk fiber without passing through the optical splitter; thus, attenuation of the optical path detection signal and the optical path detection reflection signal caused by the optical splitter is avoided, and it is ensured that the OTDR can receive the optical path detection reflection signal.

Embodiment 3

Figure 8:
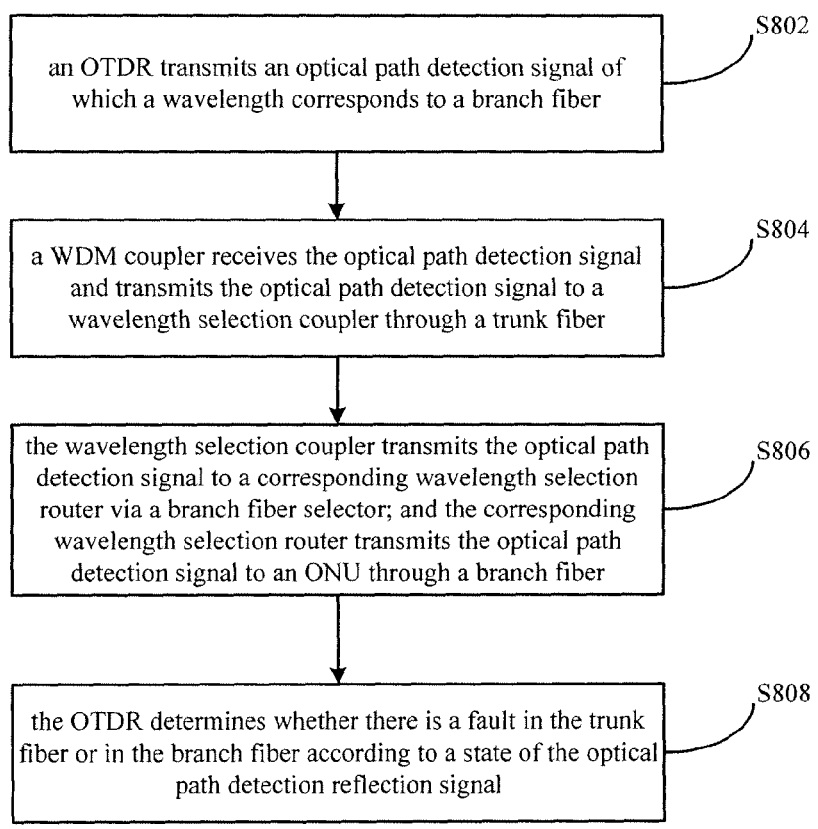
FIG. 8 shows a flowchart of a method for detecting a fiber fault in a PON according to Embodiment 3 of the disclosure.

FIG. 8 shows a flowchart of a method for detecting a fiber fault in a PON according to the embodiment of the disclosure.

This method is described by taking the implementation on the system shown in FIG. 3 for example, wherein the method comprises:

Step S802: an OTDR transmits an optical path detection signal of which a wavelength corresponds to a branch fiber;

Step S804: a WDM coupler receives the optical path detection signal and transmits the optical path detection signal to a wavelength selection coupler through a trunk fiber;

Step S806: the wavelength selection coupler transmits the optical path detection signal to a corresponding wavelength selection router through a branch fiber selector; and the corresponding wavelength selection router transmits the optical path detection signal to an ONU through a branch fiber;

wherein the optical path detection signal generates an optical path detection reflection signal during a transmission process, and the optical path detection reflection signal is transmitted to the OTDR along an optical path opposite to that of the optical path detection signal, wherein the opposite optical path refers that the optical devices the signal passes are the same but the direction of the transmission is opposite;

Step S808: the OTDR determines whether there is a fault in the trunk fiber or in the branch fiber according to a state of the optical path detection reflection signal.

The optical network module selected in this embodiment can be implemented by the method provided in the Embodiment 2. For example, the WDM coupler, the wavelength selection coupler and the wavelength selection router all adopt the same type of thin film filter, and this thin film filter reflects the signal with an optical path detection wavelength, but transmits the signal with a wavelength other than the optical path detection wavelength. No further description is provided here.

In this embodiment, the wavelength selection coupler is used to forward the optical path detection signal which is on the trunk fiber to the branch fiber selector, rather than to the optical splitter, thereby avoiding the loss of the optical path detection signal caused by the optical splitter. Meanwhile the wavelength selection router is used to forward the optical path detection reflection signal which is on the branch fiber to the branch fiber selector, thereby avoiding the loss of the optical path detection reflection signal caused by the optical splitter. As a result, the intensity of the optical path detection reflection signal is guaranteed to the greatest extent, the problem of being unable to determine whether there is a fault in the branch fiber due to the loss of optical path detection reflection signal is solved, and the specific location of the fault can be determined according to the time when an abnormality occurs to the optical path detection reflection signal.

Embodiment 4

In order to detect the fiber system of the PON intelligently, some transformations are performed on the PON first and some passive optical functional modules are added to the PON. In this embodiment, one WDM coupler is added at the OLT in accordance with the way in FIG. 3. The main function of the WDM coupler is to connect the OTDR to the trunk fiber so that the optical path detection signal (that is, the signal transmitted by the OTDR) enters the PON system and the corresponding optical path detection reflection signal can be transmitted to the OTDR through the network.

A wavelength selection coupler is inserted before the optical splitter, wherein the main function of the wavelength selection coupler is to separate out the optical path detection signal transmitted by the OTDR on the trunk fiber, transmit the separated optical path detection signal to the branch fiber selector, and transmit the optical path detection reflection signal of the branch fiber to the trunk fiber. Meanwhile, the wavelength selection coupler guarantees the normal communication of uplink and downlink signals.

A wavelength selection router is inserted behind the optical splitter and before each branch fiber, wherein the main function of the wavelength selection router is to import the optical path detection signal from the branch fiber selector to the branch fiber, and separate the optical path detection reflection signal of the branch fiber from uplink signals and transmit the optical path detection reflection signal to the branch fiber selector, and meanwhile guarantee the normal operation of uplink and downlink communications.

The branch fiber selector is placed beside the optical splitter. Referring to FIG. 6, one end of the branch fiber selector is coupled with the wavelength selection coupler, while the other end is coupled with each wavelength selection router. The main function of the branch fiber selector is to guide the optical path detection signal to the corresponding wavelength selection router and branch fiber through the splitting of the AWG according to the wavelength of the optical path detection signal, and separate the optical path detection reflection signal of the selected branch fiber from uplink signals through the connected wavelength selection router, so that the optical path detection reflection signal enters the connected AWG interface and then is guided to the wavelength selection coupler via the AWG.

Figure 9:
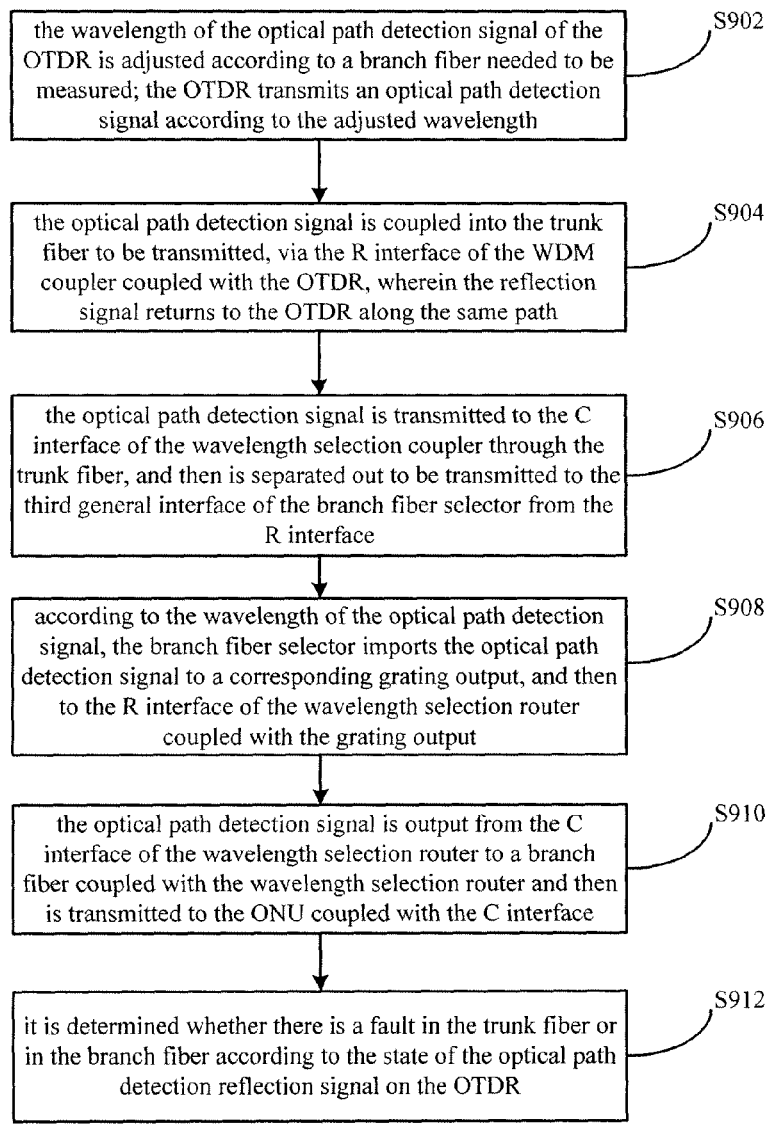
FIG. 9 shows a flowchart of a method for detecting a fiber fault in a PON according to Embodiment 4 of the disclosure.

When all these modules are coupled according to the structure shown in FIG. 3, the OTDR can detect the entire PON system intelligently. Hereinafter, the entire optical path detection process is described by taking the system shown in FIG. 3 for example. Referring to FIG. 9, the method for detecting a fiber fault in a PON comprises the following steps.

Step S902: a wavelength of a detection signal of the OTDR is adjusted according to a branch fiber needed to be measured; the OTDR transmits an optical path detection signal according to the adjusted wavelength.

When the PON needs to be detected, the OTDR is coupled with the WDM coupler in the central office first; then a corresponding optical path detection wavelength is selected for one branch fiber needed to be measured and the OTDR adjusts the wavelength of the detection signal to this wavelength. If the wavelength is at U band, the wavelength range generally is from 1625 nm to 1675 nm; if the wavelength is at C band, the wavelength range generally is from 1528 nm to 1560 nm. Here, it should be noted that, after the branch fiber selector is placed, the relationship between the grating interface of the AWG and the branch fiber is fixed, and different grating interfaces correspond to the input/output of different wavelengths. As a result, the branch fiber is identified by the optical wavelength, and the detection for different branch fibers needs to be implemented by selecting a corresponding wavelength.

After adjusting to the wavelength corresponding to the branch fiber needed to be measured, the OTDR transmits the optical path detection signal using this wavelength.

Step S904: the optical path detection signal is coupled into the trunk fiber to be transmitted, via the R interface of the WDM coupler coupled with the OTDR, wherein the reflection signal of the optical path detection signal (that is, optical path detection reflection signal) will return to the OTDR along the same path.

Step S906: the optical path detection signal is transmitted to the C interface of the wavelength selection coupler through the trunk fiber, and then is separated out to be transmitted to the general interface of the branch fiber selector (that is, AWG) from the R interface.

Step S908: according to the wavelength of the optical path detection signal, the branch fiber selector imports the optical path detection signal to a corresponding grating output, and then the optical path detection signal enters the R interface of the wavelength selection router coupled with the grating output.

Step S910: the optical path detection signal is output from the C interface of the wavelength selection router to a branch fiber coupled with the wavelength selection router and then is transmitted to the ONU coupled with the C interface.

The optical path detection reflection signal has an abnormality if the trunk fiber has any fault, and this abnormal signal will be soon discovered by the OTDR and can be quickly located.

If the trunk fiber has no fault, the optical path detection signal is transmitted to the C interface of the wavelength selection coupler, and then is separated to be output to the general interface of the AWG of the branch fiber selector from the R interface of the wavelength selection coupler; next, the optical path detection signal is imported to a corresponding grating output according to the wavelength of the optical path detection signal and then enters the R interface of the wavelength selection router coupled with the grating output; and next, the optical path detection signal is output to the connected branch fiber from the C interface of the wavelength selection router to be transmitted to the connected ONU.

The reflection signal of the optical path detection signal (that is, optical path detection reflection signal) is returned along an optical path opposite to that of the optical path detection signal, that is, the reflection signal is output from the R interface to the C interface of the wavelength selection router; then, the reflection signal reaches the grating branch input/output of the AWG of the branch fiber selector and leaves the general interface of the AWG to enter the R interface of the wavelength selection coupler coupled with the general interface of the AWG; next, the reflection signal is output from the C interface of the wavelength selection coupler to the trunk fiber, through which the reflection signal is transmitted to the C interface of the WDM coupler, and then the reflection signal is separated out to be output from the R interface of the WDM coupler to the OTDR; thus, the OTDR shows an optical path detection reflection signal of one trunk fiber plus one branch fiber each time.

Step S912: it is determined whether there is a fault in the trunk fiber or in the branch fiber according to the state of the optical path detection reflection signal on the OTDR.

If other branch fibers need to be detected, it is necessary to repeat the above steps, that is, the optical wavelength transmitted by the OTDR is adjusted to the wavelength corresponding to the branch fiber, then an optical path detection signal is transmitted and the OTDR will receive a corresponding optical path detection reflection signal, it can be determined whether there is a fault based on whether the optical path detection reflection signal is abnormal and the fault can be located. The above steps are repeated until the measurement is ended.

During the detection process, the communication between the OLT and the ONU still can be kept in a normal state. Taking the system structure shown in FIG. 3 for example, for the optical downlink, the forwarding process of the downlink signal during the detection process is described as follows: the OLT outputs a downlink signal, the WDM coupler receives the downlink signal of the OLT and imports the downlink signal onto the trunk fiber;

the wavelength selection coupler separates the optical path detection signal and the downlink signal that are transmitted by the trunk fiber, transmits the downlink signal to the optical splitter which then transmits the downlink signal to all wavelength selection routers, and the wavelength selection coupler transmits the optical path detection signal to a wavelength selection router corresponding to the signal wavelength of the optical path detection signal via the branch fiber selector;

the wavelength selection router transmits the downlink signal to an ONU connected therewith through the connected branch fiber; the optical path detection reflection signal of the branch fiber is transmitted to the OTDR along an optical path opposite to that of the optical path detection signal via the wavelength selection router.

The downlink signal output by the OLT passes through the trunk fiber to reach the wavelength selection router, after being subjected to the transmission of the WDM coupler; then the downlink signal permeates the filter to reach the optical splitter, reaches each wavelength selection router after being split by the optical splitter, permeates the filter on the wavelength selection router to reach each branch fiber and then reaches the corresponding ONU through the branch fiber.

For the optical uplink, the forwarding process of the uplink signal is as follows:

the uplink signal output by the ONU passes through the branch fiber to reach the wavelength selection router; then the uplink signal permeates the filter of the wavelength selection router to reach the optical splitter, passes through the optical splitter to reach the wavelength selection coupler, permeates the filter of the wavelength selection coupler to reach the trunk fiber, passes through the trunk fiber to reach the WDM coupler and permeates the WDM coupler to reach the OLT.

The optical network modules selected by this embodiment can be implemented by the method provided in the Embodiment 2. For example, the WDM coupler, the wavelength selection coupler and the wavelength selection router all adopt the same type of thin film filter, and this thin film filter reflects the signal with an optical path detection wavelength, but transmits the signal with a wavelength other than the optical path detection wavelength. No further description is provided here.

During the entire transmission process, the optical path detection signal of the OTDR and the optical path detection reflection signal have no interference to optical uplink and downlink. During the entire process of the optical path detection, the communication between the OLT and the ONU in the PON always keeps effective, that is, their services are not interrupted. If there is one branch fiber having a fault, the OTDR can be used to perform detection and fault location in the central office; and in the following process of repairing and restoring a normal working state, users of other branch fibers suffer no influence. This greatly reduces the maintenance cost of an operator.

The above embodiments can monitor, detect and locate the fault of the trunk fiber and all branch fibers of the PON, and detects a branch fiber by selecting a signal wavelength of the OTDR corresponding to the branch fiber. Therefore, signal overlapping is avoided on the branch fibers with equal lengths. Meanwhile, the optical path detection signal of the OTDR and the optical path detection reflection signal are transmitted back to the trunk fiber without passing through the optical splitter; in this way, no loss is caused on the optical path detection signal by the optical splitter, the detection capability and precision of the OTDR on the branch fiber is ensured, and it is effective to help an operator find the location of the fault quickly, thus maintenance time is shortened and maintenance cost is reduced. Especially when a certain branch fiber has a fault, the operator can quickly detect this branch fiber, locate the fault and perform maintenance, without influencing the normal services of other branch fibers; therefore, operation and maintenance costs of the operator are reduced.

The descriptions above are only the preferable embodiment of the disclosure, which are not used to restrict the disclosure. For those skilled in the art, the disclosure may have various changes and variations. Any amendments, equivalent substitutions, improvements, etc. within the principle of the disclosure are all included in the scope of the protection of the disclosure.

What is claimed is:

1. A system for detecting a fiber fault in a Passive Optical Network (PON), comprising:
an Optical Time Domain Reflectometer (OTDR), which is configured to transmit an optical path detection signal of which a wavelength corresponds to a branch fiber, receive an optical path detection reflection signal, and determine whether there is a fault in a trunk fiber or in the branch fiber according to a state of the optical path detection reflection signal;
a Wavelength Division Multiplexing (WDM) coupler, which is configured to import the optical path detection signal onto the trunk fiber and transmit the optical path detection reflection signal transmitted by the trunk fiber to the OTDR;
a wavelength selection coupler, which is configured to transmit the optical path detection signal which is on the trunk fiber to a branch fiber selector and import the optical path detection reflection signal, which is received from the branch fiber selector, back onto the trunk fiber;
the branch fiber selector, which is configured to transmit the optical path detection signal to a corresponding wavelength selection router and transmit the optical path detection reflection signal, which is transmitted from the wavelength selection router, to the wavelength selection coupler; and
the wavelength selection router, which is coupled with an Optical Network Unit (ONU) corresponding to the wavelength selection router through a branch fiber, and is configured to transmit the optical path detection signal to the ONU and transmit the optical path detection reflection signal which is on the branch fiber to the branch fiber selector;
wherein the branch fiber selector is an Arrayed-Waveguide Grating (AWG), and the AWG comprises:
a general interface, which is coupled with the wavelength selection coupler;
a plurality of grating branch inputs/outputs, which are coupled with the corresponding wavelength selection router on each branch fiber and are configured to transmit the optical path detection signal to the corresponding wavelength selection router according to the wavelength of the optical path detection signal.

2. The system according to claim 1, wherein
the WDM coupler is further configured to receive a downlink signal of an Optical Line terminal (OLT) and import the downlink signal onto the trunk fiber, separate the optical path detection reflection signal and an uplink signal that are transmitted by the trunk fiber, and transmit the uplink signal to the OLT;
the wavelength selection coupler is further configured to separate the optical path detection signal and the downlink signal that are transmitted by the trunk fiber, transmit the downlink signal to an optical splitter, receive the uplink signal transmitted by the optical splitter and transmit the uplink signal to the trunk fiber;
the system further comprises: the optical splitter, which is configured to transmit the downlink signal to all wavelength selection routers, receive uplink signal transmitted by each wavelength selection router and transmit the uplink signal to the wavelength selection coupler;
the wavelength selection router is further configured to transmit the downlink signal to the ONU which is coupled with the wavelength selection router, separate the optical path detection reflection signal and uplink signal of the ONU, and transmit the separated uplink signal to the optical splitter.

3. The system according to claim 2, wherein the WDM coupler is a first optical filter, and the first optical filter comprises:
a first interface, which is coupled with the OLT and is configured to transmit the uplink signal and the downlink signal;
a second interface, which is coupled with the OTDR and is configured to: transmit the optical path detection signal to the trunk fiber and transmit the optical path detection reflection signal to the OTDR; and
a general interface, which is coupled with the trunk fiber.

4. The system according to claim 2, wherein the wavelength selection coupler is a second optical filter, and the second optical filter comprises:
a first interface, which is coupled with the optical splitter and is configured to transmit the uplink signal and the downlink signal;
a second interface, which is coupled with the branch fiber selector and is configured to: transmit the optical path detection signal to the branch fiber selector and transmit the optical path detection reflection signal to the trunk fiber; and
a general interface, which is coupled with the trunk fiber.

5. The system according to claim 2, wherein the wavelength selection router is a third optical filter, and the third optical filter comprises:
a first interface, which is coupled with the optical splitter and is configured to transmit the uplink signal and the downlink signal;
a second interface, which is coupled with the branch fiber selector and is configured to: receive the optical path detection signal and transmit the optical path detection reflection signal to the branch fiber selector; and
a general interface, which is coupled with the ONU through the branch fiber and is configured to: transmit the optical path detection signal received by the second interface to the ONU and receive the optical path detection reflection signal from the branch fiber.

6. The system according to claim 3, wherein the first optical filter is a thin film filter, and the thin film filter reflects a signal with an optical path detection wavelength and transmits a signal with a wavelength other than the optical path detection wavelength.

7. The system according to claim 4, wherein the second optical filter is a thin film filter, and the thin film filter reflects a signal with an optical path detection wavelength and transmits a signal with a wavelength other than the optical path detection wavelength.

8. The system according to claim 5, wherein the third optical filter is a thin film filter, and the thin film filter reflects a signal with an optical path detection wavelength and transmits a signal with a wavelength other than the optical path detection wavelength.

9. A method for detecting fiber fault in a Passive Optical Network (PON), comprising:
- an Optical Time Domain Reflectometer (OTDR) transmitting an optical path detection signal of which a wavelength corresponds to a branch fiber;
- a Wavelength Division Multiplexing (WDM) coupler receiving the optical path detection signal and transmitting the optical path detection signal to a wavelength selection coupler through a trunk fiber;
- the wavelength selection coupler transmitting the optical path detection signal to a corresponding wavelength selection router through a branch fiber selector; the corresponding wavelength selection router transmitting the optical path detection signal to an Optical Network Unit (ONU) through a branch fiber;
- wherein the optical path detection signal generates an optical path detection reflection signal during a transmission process, and the optical path detection reflection signal is transmitted to the OTDR along an optical path opposite to that of the optical path detection signal;
- the OTDR determining whether there is a fault in the trunk fiber or in the branch fiber according to a state of the optical path detection reflection signal;
- wherein the branch fiber selector is an Arrayed-Waveguide Grating (AWG), and the AWG comprises:
- a general interface, which is coupled with the wavelength selection coupler;
- a plurality of grating branch inputs/outputs, which are coupled with the corresponding wavelength selection router on each branch fiber and are configured to transmit the optical path detection signal to the corresponding wavelength selection router according to the wavelength of the optical path detection signal.

10. The method according to claim 9, wherein
- a process of the WDM coupler receiving the optical path detection signal further comprises: the WDM coupler receiving a downlink signal of an OLT and importing the downlink signal onto the trunk fiber;
- a process of the wavelength selection coupler transmitting the optical path detection signal to the corresponding wavelength selection router through the branch fiber selector comprises: the wavelength selection coupler separating the optical path detection signal and the downlink signal that are transmitted by the trunk fiber, transmitting the downlink signal to an optical splitter which then transmits the downlink signal to all wavelength selection routers, and transmitting the optical path detection signal to the wavelength selection router corresponding to the wavelength of the optical path detection signal through the branch fiber selector;
- a process of the wavelength selection router transmitting the optical path detection signal to the ONU through the branch fiber comprises: the wavelength selection router transmitting, through a connected branch fiber, the downlink signal to the ONU coupled with the wavelength selection router.

11. The method according to claim 10, further comprising:
- the wavelength selection router separating the optical path detection reflection signal and an uplink signal of the ONU, wherein the separated uplink signal is transmitted to the OLT along an optical path opposite to that of the downlink signal.

* * * * *